(12) United States Patent
Long

(10) Patent No.: US 11,395,758 B2
(45) Date of Patent: Jul. 26, 2022

(54) PESSARY FOR TRANSVAGINAL HAEMOSTASIS

(71) Applicant: Kaohsiung Medical University, Kaohsiung (TW)

(72) Inventor: Cheng-Yu Long, Kaohsiung (TW)

(73) Assignee: KAOHSIUNG MEDICAL UNIVERSITY, Kaohsiung (TW)

(*) Notice: Subject to any disclaimer, the term of this patent is extended or adjusted under 35 U.S.C. 154(b) by 760 days.

(21) Appl. No.: 16/338,175

(22) PCT Filed: Sep. 30, 2016

(86) PCT No.: PCT/CN2016/101006
§ 371 (c)(1),
(2) Date: Mar. 29, 2019

(87) PCT Pub. No.: WO2018/058499
PCT Pub. Date: Apr. 5, 2018

(65) Prior Publication Data
US 2020/0022836 A1    Jan. 23, 2020

(51) Int. Cl.
*A61F 6/08* (2006.01)
*A61F 6/16* (2006.01)
*A61B 17/12* (2006.01)

(52) U.S. Cl.
CPC .......... *A61F 6/08* (2013.01); *A61B 17/12136* (2013.01); *A61B 2017/12004* (2013.01)

(58) Field of Classification Search
CPC .... A61F 6/08; A61F 5/16; A61F 6/146; A61F 2/004; A61B 17/425; A61B 17/12136; A61B 2017/12004
See application file for complete search history.

(56) References Cited

U.S. PATENT DOCUMENTS 2,638,093 A * 5/1953 Kulick ............... A61F 5/485
  128/DIG. 25
2,849,002 A * 8/1958 Oddo ................ A61M 25/1011
  606/192

(Continued)

FOREIGN PATENT DOCUMENTS

CN    205234559 U    5/2016
DE    19816349 A1    10/1999
(Continued)

*Primary Examiner* — Camtu T Nguyen
(74) *Attorney, Agent, or Firm* — WPAT, PC

(57) ABSTRACT

Disclosed is a pessary for transvaginal haemostasis, wherein the radial dimension of a balloon body can be changed to form a relatively large pressure on a vaginal wall, therefore achieving the effect of high-pressure haemostasis. The pessary for transvaginal haemostasis comprises: the balloon body, being made of an expandable material, the balloon body having a cavity, the cavity having a filling hole so that a fluid can be filled into or drawn out of the cavity through the filling hole, the balloon body having a first end and a second end, the balloon body having at least one hollow passage, the passage running through the first end and the second end of the balloon body and not being in communication with the cavity, an outer surface of the balloon body having at least one channel, and the channel also running through the first end and the second end of the balloon body; and a support body having a coupling end and a support end, the coupling end being coupled to the second end of the balloon body, the support body having a through hole in communication with the passage, and the peripheral surface of the support body having at least one recessed portion corresponding to the channel.

10 Claims, 2 Drawing Sheets

(56) References Cited

U.S. PATENT DOCUMENTS

| | | | | | |
|---|---|---|---|---|---|
| 4,850,953 | A | * | 7/1989 | Haber | A61F 2/0013 600/32 |
| 5,041,077 | A | * | 8/1991 | Kulick | A61F 2/005 128/DIG. 25 |
| 5,603,685 | A | * | 2/1997 | Tutrone, Jr. | A61F 2/005 128/885 |
| 10,463,530 | B2 | | 11/2019 | Booher, Sr. | |
| 2013/0138134 | A1 | | 5/2013 | Elman et al. | |

FOREIGN PATENT DOCUMENTS

| | | |
|---|---|---|
| WO | WO2011141866 A2 | 11/2011 |
| WO | WO2014081336 A1 | 5/2014 |

* cited by examiner

PESSARY FOR TRANSVAGINAL HAEMOSTASIS

BACKGROUND OF THE INVENTION

1. Field of the Invention

The invention relates to a device for transvaginal haemostasis, in particular to a pessary for transvaginal haemostasis with a hemostatic function in which the radial dimension of the balloon body of the pessary can be changed.

2. Description of the Related Art

Pelvic organs include a uterus, a vagina, a bladder and an intestine. Uterine prolapse is the prolapse of one of the pelvic organs, and is particularly referred to the situation that the uterus prolapses into the vagina and even out of the body. Uterine prolapse is caused by increased abdominal pressure and reduced support of the pelvis cavity, which mainly happens to women who suffer from a long-term cough, are pregnant or obese, or are on their feet for a long time or under a vaginal surgery. During the pregnancy, since the abdomen becomes larger, the abdominal pressure increases, and it is required to squeeze the fetus out of the vaginal opening of the pelvis cavity during parturition, the support of the pelvis cavity tends to reduce. On the other hand, the vaginal surgery causes damage to the muscles and nerves of the vagina, which also leads to reduction in the support of the pelvic cavity. Thus, uterine prolapse is commonly seen in women who are pregnant or under a viginal surgery, or have multiple births.

The most common approaches to treat the uterine prolapse is to cut the entire uterus or to push the uterus back to the original position by a vaginal surgery. The risk of a hysterectomy is low and the recovery is quick, but it puts a lot of pressure on the patient. If the uterus is pushed back to the original position by the vaginal surgery, the pressure of the patient is small, but the recurrence rate of the uterine prolapse is high. Therefore, in order to prevent a uterine prolapse after birth or a recurrence of the uterine prolapse after surgery, the uterine prolapse after birth or vaginal surgery can be prevented by inserting a pessary into the vagina to support the uterus along with performing a pelvic floor exercise to train the muscles of the pelvic organs and to therefore increase the support force of the pelvic cavity.

The existing pessaries can support the uterus and prevent uterine prolapse only after parturition or vaginal surgery, but cannot achieve hemostasis after parturition or vaginal surgery. In general, hemostasis is achieved by inserting the existing pessary into the vagina and filling the vagina with a filler to stop bleeding, which leads to a complex procedure and cannot stop bleeding in time. Because the existing pessaries are in a variety of dimensions, the doctor needs to spend a lot of time on the selection of the dimension. This will, particularly in the case where hemostasis is urgently required, impede the health of the woman or leads to a threat to the life of the woman after parturition or under vaginal surgery, while the patient also needs to spend a lot of money purchasing the pessaries with different dimensions for testing purposes.

Accordingly, it is necessary to improve the existing pessaries to reduce the time on selecting a pessary with a proper dimension as well as the cost in using the pessaries of various dimensions, while reducing the complexity in stopping the bleeding after the surgery and achieving a timely stop of the bleeding.

SUMMARY OF THE INVENTION

In order to solve the problems above, the invention aims to provide a pessary for transvaginal haemostasis, the dimension of the pessary can be changed according to needs, and the pessary has a hemostatic function.

The invention provides a pessary for transvaginal haemostasis, including a balloon body and a support body. The balloon body is made of an expandable material. The balloon body is provided with a cavity having a filling hole to permit fluid to be filled into or drawn out of the cavity through the filling hole. The balloon body is provided with a first end and a second end. The balloon body is provided with at least one hollow passage running through the first end and the second end of the balloon body and not intercommunicating with the cavity. An outer surface of the balloon body is provided with at least one channel also running through the first end and the second end of the balloon body. The support body is with an engaging end and a support end. The engaging end is engaged with the second end of the balloon body. The support body is provided with a through-hole intercommunicating with the passage. An outer surface of the support body is provided with at least one concave portion corresponding to the channel.

The outer surface of the balloon body is provided with at least one ring protrusion, therefore the balloon body can form a better positioning effect with an inner wall of the vagina.

A cross section of the ring protrusion is in a circular shape or a semi-circular shape, therefore reducing the damage to the vagina portion without uncomfortable feeling upon the insertion and withdrawal.

A radial dimension of the balloon body after a radial expansion is larger than the radial dimension of the support body, therefore the balloon body can exert a larger pressure effect on the vaginal wall.

The outer surface of the support body is in flush connection with the outer surface of the balloon body, therefore reducing the damage to the vagina portion without uncomfortable feeling upon the pessary is inserted into the vagina portion.

The outer surface of the support body is provided with an angle-guiding portion at the support end, therefore the pessary is inserted into the vagina portion with a smooth effect.

The through-hole of the support body is provided with an angle-guiding portion at the support end, therefore the pessary is inserted into the vagina portion with a smooth effect.

A surface of the concave portion is in flush connection with the channel of the balloon body, therefore reducing the damage to the vagina portion without uncomfortable feeling upon the pessary is inserted into the vagina portion.

The through-hole is in flush connection with a tube wall of the passage, therefore a uterine secretion can be smoothly guided out of the through-hole and the passage.

The filling hole is formed at the first end of the balloon body, therefore the fluid can be conveniently filled into the balloon body.

Accordingly, the pessary for transvaginal haemostasis of the invention can be positioned at a predetermined position in the vagina through the balloon body. In addition, since the balloon body and the support body jointly support the uterus, the support for the uterus is assisted to prevent the pessary from coming off. In addition, when the pessary for transvaginal haemostasis is used after surgery, not only the uterine prolapse can be prevented, but also pressure can be exerted on the vaginal wall by the balloon body to achieve hemostasis under high pressure. Furthermore, the pessary for transvaginal haemostasis of the invention permits the balloon body to be filled with a proper amount of the fluid according to different requirements of the user. This can achieve the advantages of quick adjustment in the dimension of the balloon body, the reduction of time on selecting a pessary with a proper dimension, as well as the reduction of the cost for purchasing the pessaries of various dimensions.

DETAILED DESCRIPTION OF THE INVENTION

In order to make the above and other objects, features and advantages of the invention more comprehensible, the preferred embodiment of the present invention is described in conjunction with the accompanying drawings in detail below.

Figure 1:
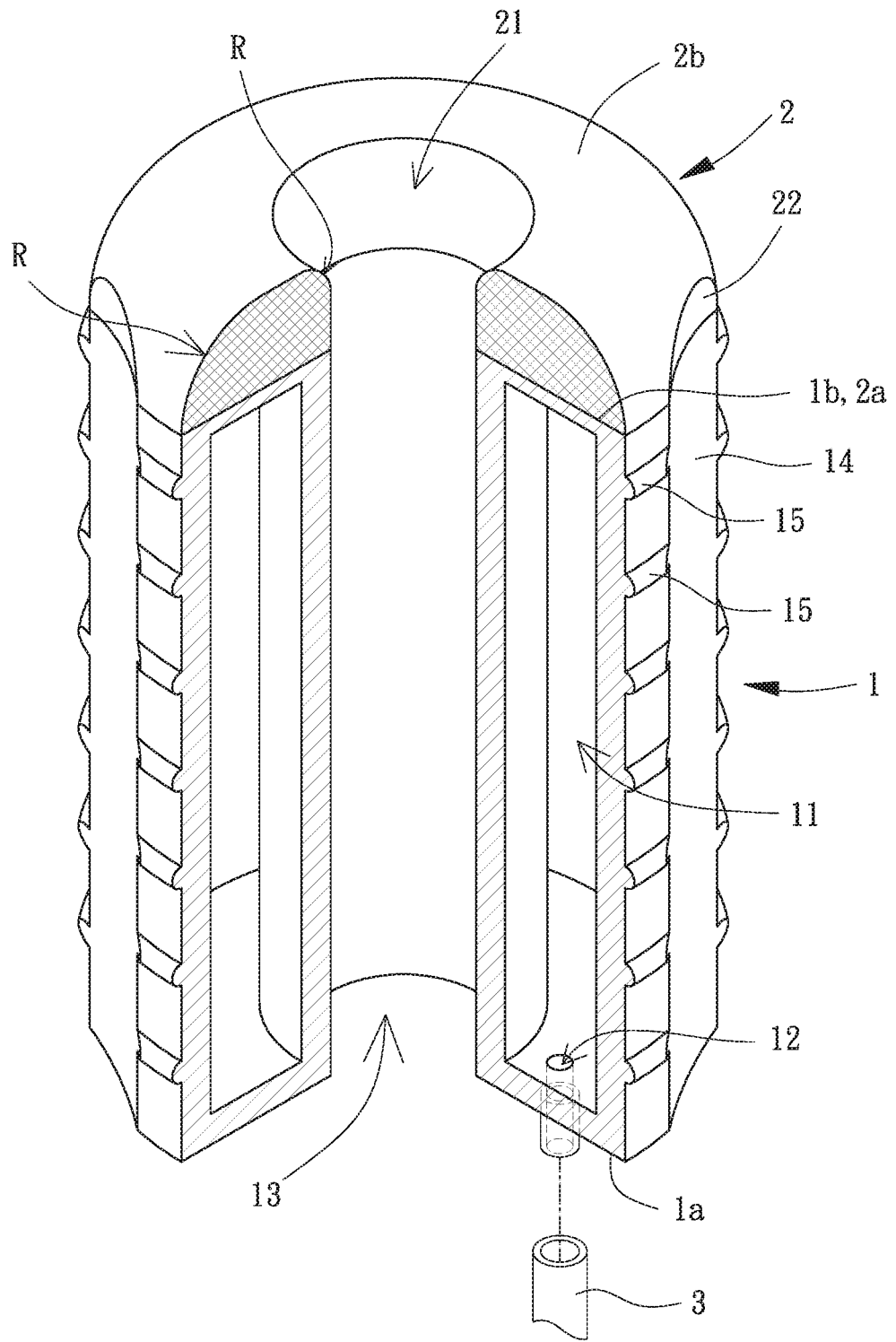
FIG. 1 is a partial cross sectional view of the present invention.

Please refer to FIG. 1, which is a preferred embodiment of the invention. The pessary for transvaginal haemostasis includes a balloon body 1 and a support body 2 engaged with one end of the balloon body 1.

The balloon body 1 is made of an expandable material such as rubber, silicone or the like. The balloon body 1 has a cavity 11 with a filling hole 12, such that the fluid can flow into the cavity 11 through the filling hole 12 and fill the cavity 11 to cause radial expansion of the balloon body 1, or the fluid is guided out of the chamber 11 to change the radial dimension of the balloon body 1. The balloon body 1 has a first end 1a and a second end 1b. The filling hole 12 is preferably located at the first end 1a of the balloon body 1, so that the fluid can be conveniently filled into the balloon body 1. The balloon body 1 forms a circular shape having at least one hollow passage 13 not intercommunicating with the cavity 11. The balloon body 1 preferably forms a shape resembling a swim ring. The at least one passage 13 runs through the first end 1a and the second end 1b of the balloon body 1. The uterine secretion can flow out of and discharge from the first end 1a of the body through the passage 13. The outer surface of the balloon body 1 is provided with at least one recessed channel 14 also running through the first end 1a and the second end 1b of the balloon body 1. The channel 14 can be used for guiding the secretion of the vaginal inner wall out of the first end 1a. The outer surface of the balloon body 1 is preferably further provided with at least one ring protrusion 15 between the first end 1a and the second end 1b. A better positioning effect with the inner wall of the vagina can be provided through the at least one ring protrusion 15. The cross section of the at least one ring protrusion 15 is preferably in a circular shape or a semi-circular shape, therefore reducing the damage to the vagina portion without uncomfortable feeling upon the insertion and withdrawal.

The support body 2 is made of silicone or the like. The support body 2 is provided with an engaging end 2a and a support end 2b. The engaging end 2a of the support body 2 is engaged with the second end 1b of the balloon body 1. The support body 2 is provided with at least one through-hole 21 intercommunicating with the passage 13 of the balloon body 1. The through-hole 21 runs through the engaging end 2a and the support end 2b, and is in flush connection with the tube wall of the passage 13 to permit the uterine secretion to be smoothly guided out of the through-hole 21 and the passage 13. The outer surface of the support body 2 is provided with at least one concave portion 22 corresponding to the channel(s) 14 of the balloon body 1, in which a surface of the concave portion 22 is in flush connection with the channel(s) 14 of the balloon body 1, therefore permitting the secretion of the inner wall of the vagina to be smoothly guided out of the concave portion 22 and the channel 14. The outer surface of the support body 2 is preferably in flush connection with the outer surface of the balloon body 1. Both the outer surface and the through-hole 21 of the support body 2 form an angle-guiding portion R at the support end 2b to achieve smooth insertion of the pessary into the vagina portion without causing an uncomfortable feeling, therefore reducing the damage to the vagina portion.

Figure 2:
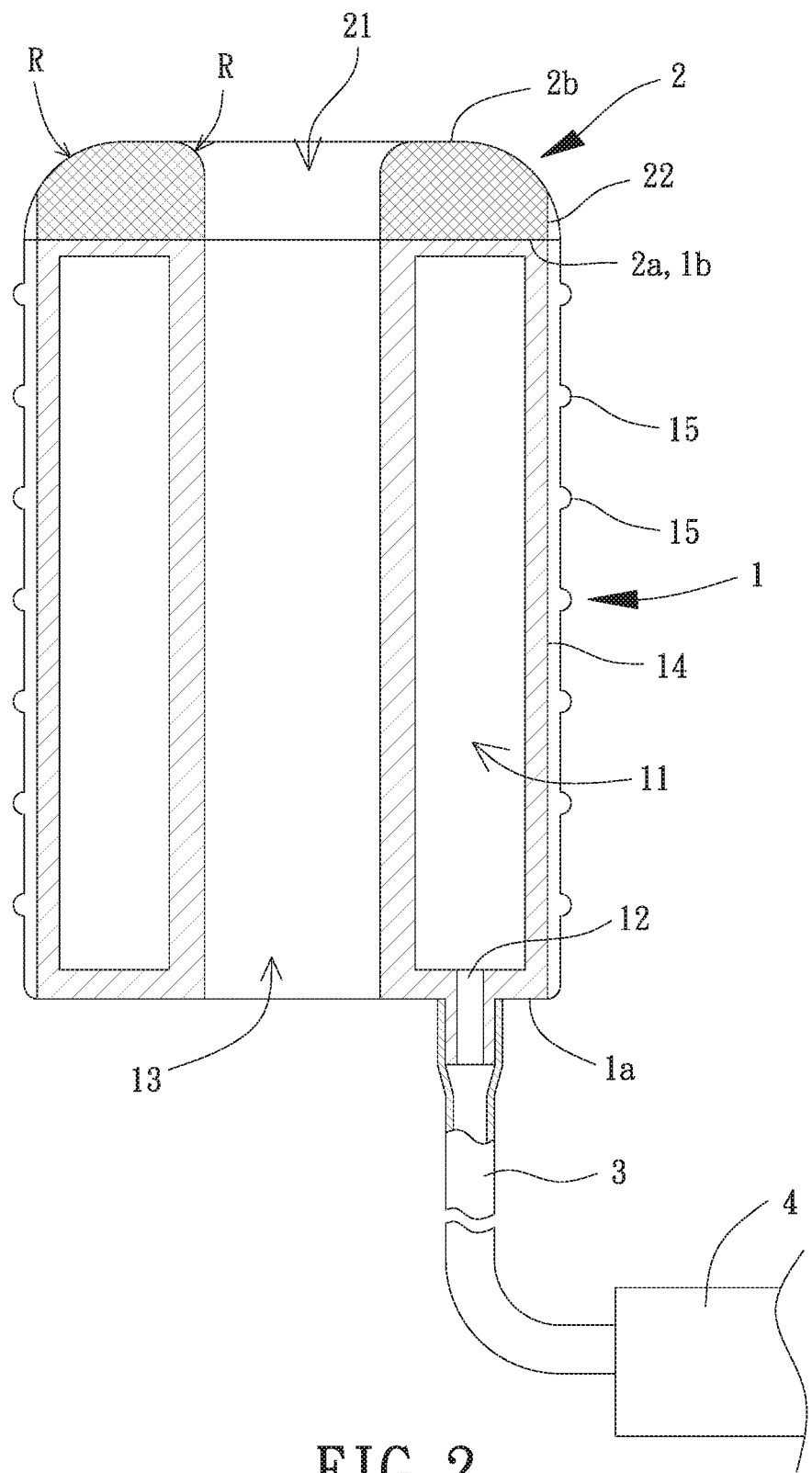
FIG. 2 shows a use of the present invention.

Please refer to FIG. 2 showing a use of an embodiment of the invention. The combined balloon body 1 and support body 2 can be rapidly placed in a predetermined position in the vagina. A guide tube 3 is connected to the filling hole 12 of the balloon body 1, and the fluid is filled into the cavity 11 of the balloon body 1 by a filling device 4, such as a pump, to increase the volume of the balloon body 1 to a proper dimension. The proper dimension is determined according to the degree of uterine prolapse and the user's requirements such as whether the hemostasis is needed and the dimension of the vagina of the user. The radial dimension of the balloon body 1 after expansion can be larger than the radial dimension of the support body 2, so that the balloon body 1 can exert larger pressure on the vaginal wall to permit the balloon body 1 and the support body 2 to jointly support the uterus. In addition, the filled balloon body 1 can exert a larger pressure on the vaginal wall to achieve hemostasis under high pressure.

Preferably, the fluid can be gas to reduce the weight of the pessary and to prevent the pessary from coming off. In addition, before the pessary for transvaginal haemostasis is placed into the vagina of the user, the fluid can be filled in advance to expand the balloon body 1 to a pre-filling dimension smaller than the proper dimension for convenient insertion of the pessary. After the pessary for transvaginal haemostasis is placed into the vagina of the user, the balloon body 1 is expanded to the proper dimension. After the balloon body 1 is filled, the total amount of the fluid filled can also be recorded. Thus, in a repeated use, the total amount of the fluid can be directly filled into the balloon body 1 to expand the balloon body 1 to the proper dimension.

In summary, the pessary for transvaginal haemostasis of the invention can be positioned at a predetermined position in the vagina through the balloon body. In addition, since the balloon body and the support body jointly support the uterus, the support for the uterus is assisted to prevent the pessary from coming off. In addition, when the pessary for transvaginal haemostasis is used after surgery, not only the uterine prolapse can be prevented, but also pressure can be exerted on the vaginal wall by the balloon body to achieve hemostasis under high pressure. Furthermore, the pessary for transvaginal haemostasis of the invention permits the balloon body to be filled with a proper amount of the fluid according to different requirements of the user. This can achieve the advantages of quick adjustment in the dimension of the balloon body, the reduction of time on selecting a pessary with a proper dimension, as well as the reduction of the cost for purchasing the pessaries of various dimensions.

What is claimed is:

1. A pessary for transvaginal haemostasis, comprising:
    a balloon body made of an expandable material, wherein the balloon body is provided with a cavity having a filling hole to permit fluid to be filled into or drawn out of the cavity through the filling hole, wherein the balloon body is provided with a first end and a second end, wherein the balloon body is provided with at least one hollow passage running through the first end and the second end of the balloon body and not intercommunicating with the cavity, and wherein an outer surface of the balloon body is provided with at least one channel also running through the first end and the second end of the balloon body; and
    a support body with an engaging end and a support end, wherein the engaging end is engaged with the second end of the balloon body, wherein the support body is provided with a through-hole intercommunicating with the at least one hollow passage, and wherein an outer surface of the support body is provided with at least one concave portion corresponding to the at least one channel.

2. The pessary for transvaginal haemostasis as claimed in claim 1, wherein the outer surface of the balloon body is provided with at least one ring protrusion.

3. The pessary for transvaginal haemostasis as claimed in claim 2, wherein a cross section of the at least one ring protrusion is in a circular shape or a semi-circular shape.

4. The pessary for transvaginal haemostasis as claimed in claim 1, wherein a radial dimension of the balloon body after radial expansion is larger than a radial dimension of the support body.

5. The pessary for transvaginal haemostasis as claimed in claim 1, wherein the outer surface of the support body is in flush connection with the outer surface of the balloon body.

6. The pessary for transvaginal haemostasis as claimed in claim 1, wherein the outer surface of the support body is provided with an angle-guiding portion at the support end.

7. The pessary for transvaginal haemostasis as claimed in claim 1, wherein the through-hole of the support body is provided with an angle-guiding portion at the support end.

8. The pessary for transvaginal haemostasis as claimed in claim 1, wherein a surface of the at least one concave portion is in flush connection with the at least one channel of the balloon body.

9. The pessary for transvaginal haemostasis as claimed in claim 1, wherein the through-hole is in flush connection with a tube wall of the at least one hollow passage.

10. The pessary for transvaginal haemostasis as claimed in claim 1, wherein the filling hole is formed at the first end of the balloon body.

* * * * *